United States Patent [19]

Varsanyi

[11] 3,968,206
[45] July 6, 1976

[54] THIOPHOSPHORIC ACID AMIDES AS NEMATOCIDES, INSECTICIDES AND ACARICIDES

[75] Inventor: Denis Varsanyi, Arlesheim, Switzerland

[73] Assignee: Ciba-Geigy Corporation, Ardsley, N.Y.

[22] Filed: Mar. 3, 1975

[21] Appl. No.: 554,355

Related U.S. Application Data

[62] Division of Ser. No. 377,465, July 9, 1973, Pat. No. 3,883,556.

[30] Foreign Application Priority Data

July 13, 1972 Switzerland........................ 10529/72

[52] U.S. Cl............................. 424/200; 260/326.61
[51] Int. Cl.²............................................ A01N 9/36
[58] Field of Search..................................... 424/200

[56] References Cited
UNITED STATES PATENTS 3,511,633  5/1970  Kleiman et al........................... 31/67
3,794,724  2/1974  O'Melia................................. 424/200
3,883,556  5/1975  Varsanyi............................... 424/200

*Primary Examiner*—V. D. Turner
*Attorney, Agent, or Firm*—Frederick H. Rabin; Harry Falber

[57] ABSTRACT

Thiophosphoric acid amides of the formula

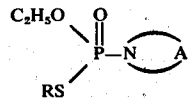

wherein R represents the n-propyl or n-butyl radical, and A represents the ethylene, 1-methylethylene, 1,1-dimethylethylene, 2-butenylene or 2-pentenylene radical are very effective agents for combating nematodes, insects and members of the order acarina.

3 Claims, No Drawings

THIOPHOSPHORIC ACID AMIDES AS NEMATOCIDES, INSECTICIDES AND ACARICIDES

This is a division of application Ser. No. 377,465 filed on July 9, 1973, now U.S. Pat. No. 3,883,556.

The present invention relates to thiophosphoric acid amides, process for their manufacture, and to their use in pest control.

The compounds correspond to the formula

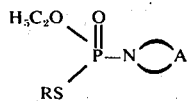

wherein R represents the n-propyl or n-butyl radical and A represents the ethylene, 1-methylethylene, 1,1-dimethylethylene, 2-butenylene or 2-pentenylene radical.

The compounds comprised by formula I possess very good pesticidal properties. To be particularly highlighted are the compounds of the formula I, in which A represents the 2-butenylene or 2-pentenylene radical.

The compounds of the formula I can be manufactured by the following methods which are known per se:

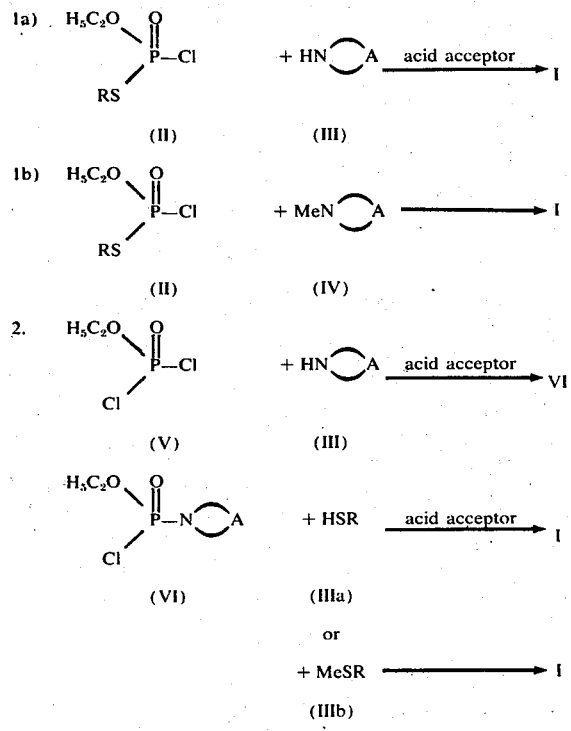

In the formulae II to VI R and A have the meanings given for the formula I, Me represents an alkali metal, in particular sodium or potassium, an ammonium or alkylammonium group.

Suitable acid agents are: tertiary amines, e.g., trialkylamines, pyridine, dialkylanilines; inorganic bases, e.g., hydrides, hydroxides, and carbonates and bicarbonates of alkali metals and alkaline earth metals. It is sometimes necessary to use catalysts in the reactions, for example copper or copper chloride. Processes (1a), (1b) and (2) are carried out at a reaction temperature between $-2°$ to $130°C$, at normal pressure, and in solvents or diluents. Optionally it is also possible to carry out the reactions in an atmosphere of inert gas, for example in a nitrogen atmosphere.

Examples of suitable solvents or diluents are: water, ether and ethereal compounds, e.g., diethyl ether, dipropyl ether, dioxan, tetrahydrofuran; amides, e.g., N,N-dialkylated carboxylic amides; aliphatic, aromatic, and halogenated hydrocarbons, in particular benzene, toluene, xylene, chloroform, chlorobenzene; nitriles, e.g., acetonitrile; dimethyl sulphoxide; ketones, for example acetone or methyl ethyl ketone.

The starting materials of the formulae II, III, and V can be manufactured by known methods.

The compounds of the formula I possess insecticidal, acaricidal, and, in particular, nematocidal properties which are superior to those of known, analogous compounds. The compounds according to the invention can therefore be used for combating, e.g., the following species of plant pathogenic nematodes:

Meloidogyne, Heterodera, Ditylenchus, Pratylenchus, Paratylenchus, Anguina, Belonolaismus, Trichodorus, Longidorus, Aphelenchoides.

The insecticidal or acaricidal action can be substantially broadened and adapted to given circumstances by addition of other insecticides and/or acaricides.

The compounds of the formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilizers.

For application, the compounds of the formula I may be processed to dusts, emulsion concentrates, granules, dispersions, sprays, to solutions, or suspensions, in the conventional formulation which is commonly employed in application technology.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:

Solid forms:
Dusts, tracking agents, granules, coated granules, impregnated granules and homogeneous granules.

Liquid forms:
 a. active substances which are dispersible in water: wettable powders, pasts, emulsions;
 b. solutions.

To manufacture solid forms (dusts, tracking agents), the active substances are mixed with solid carriers. Suitable carriers are, for example: kaolin, talcum, bolus, loess, chalk, limestone, ground limestone, attapulgite, dolomite, diatomaceous earth, precipitated silica, alkaline earth silicates, sodium and potassium aluminium silicates (feldspar and mica), calcium and magnesium sulphates, magnesium oxide, ground synthetic materials, fertilizers, for example ammonium sulphate, ammonium phosphate, ammonium nitrate, urea, ground vegetable products, such as corn meals, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SiO_2$, granicalcium, bentonite, etc., and then evaporating the solvent.

Polymer granules can be manufactured by impregnating finished, porous polymer granules (urea/formaldehyde, polyacrylonitrile, polyester or others) which have a specific surface area and a favorable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomizers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e., wettable powders, pastes and emulsifiable concentrates, are agents which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove, in such a manner that, the size of the solid particles does not exceed 0.02 to 0.04mm in wettable powders, and 0.03mm in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350°C. The solvents must be practically odorless, not phytotoxic, and inert to the active substances.

Furthermore, the agents according to the invention can be applied in the form of solutions. For this purpose the active substances, or several active substances of the general formula I, are dissolved in suitable organic solvents, mixtures of solvents or in water. Aliphatic and aromatic hydrocarbons, chlorinated derivatives thereof, alkyl naphthalenes, and mineral oils, singly or in admixture with each other, can be used as organic solvents.

The content of active substance in the above described agents is between 0.1 to 95%.

The active substances of the formula I can, for example, be formulated as follows:

Dusts

The following substances are used to manufacture (a) a 5% and (b) a 2% dust:
a. 5 parts of active substance
   95 parts of talcum
b. 2 parts of active substance
   1 part of highly disperse silicic acid
   97 parts of talcum.

The active substances are mixed with the carriers and ground.

Granules

The following substances are used to produce 5% granules:
  5 parts of active substance,
  0.25 parts of epichlorohydrin,
  0.25 parts of cetyl polyglycol ether,
  3.50 parts of polyethylene glycol,
  91 parts of kaolin (particle size 0.3–0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder

The following constituents are used for the preparation of (a) a 40%, (b) and (c) a 25%, and (d) a 10% wettable powder:
a. 40 parts of active substance,
   5 parts of sodium lignin sulphonate,
   1 part of sodium dibutyl-naphthalene sulphonate,
   54 parts of silicic acid.
b. 25 parts of active substance,
   4.5 parts of calcium lignin sulphonate,
   1.9 parts of Champagne chalk/hydroxyethyl cellulose mixture (1:1),
   1.5 parts of sodium dibutyl naphthalene sulphonate, 19.5 parts of silicic acid,
19.5 parts of Champagne chalk,
28.1 parts of kaolin.
c. 25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin.
d. 10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:
a. 10 parts of active substance,
3.4 parts of epoxidized vegetable oil,
13.4 parts of a combination emulsifier consisting of fatty alcohol polyglycol ether and alkylarylsulphonate calcium salt,
40 parts of dimethylformamide,
43.2 parts of xylene.
b. 25 parts of active substance,
2.5 parts of epoxidized vegetable oil,
10 parts of an alkylarylsulphonate/fatty alcohol-polyglycol ether mixture,
5 parts of dimethylformamide,
57.5 parts of xylene.

From these concentrates it is possible to produce, by dilution with water, emulsions of any desired concentration.

Spray

The following constituents are used to prepare a 5% spray:
5 parts of active substance,
1 part of epichlorohydrin,
94 parts of benzine (boiling limits 160° – 190°C).

EXAMPLE 1

A solution of 29.6 g of O-ethyl-S-n-propylthiophosphoric chloride in 50 ml of chloroform is added dropwise at 3° to 5°C within 2 hours to a solution of 12.5 g of pyroline and 13.7 g of triethylamine in 100 ml of chloroform. The reaction mixture is heated slowly (2 hours) to room temperature and then stirred for 18 hours. The mixture is then concentrated in vacuo, the residue taken up in ether, and the precipitated triethylamine chlorohydrate is isolated. The filtrate is washed until neutral and the solvent distilled off to leave as residue O-ethyl-S-n-propyl-N,N-2-butenylene-thiophosphoric acid amide: $n_D^{25} = 1.4990$ (compound 1).

EXAMPLE 2

A solution of 41.4 g of O-ethyl-S-n-propylthiophosphoric chloride in 100 ml of chloroform is added dropwise in a nitrogen atmosphere at 5°–10°C to a solution of 8.6 g of ethylene imine and 20.2 g of triethylamine in 300 ml of anhydrous chloroform. The mixture is stirred for 1 hour and subsequently evaporated. The residue is taken up in 350 m of diethyl ether and the precipitated triethylamine chlorohydrate is filtered off. The filtrate is evaporated. Molecular distillation yields the compound of the formula

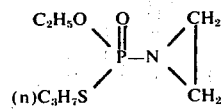

with a boiling point of 65°–60°C at $10^{-4}$ Torr and a refractive index of $n_D^{24} = 1.4898$ (compound 2).

The following compounds are also manufactured in analogous manner:

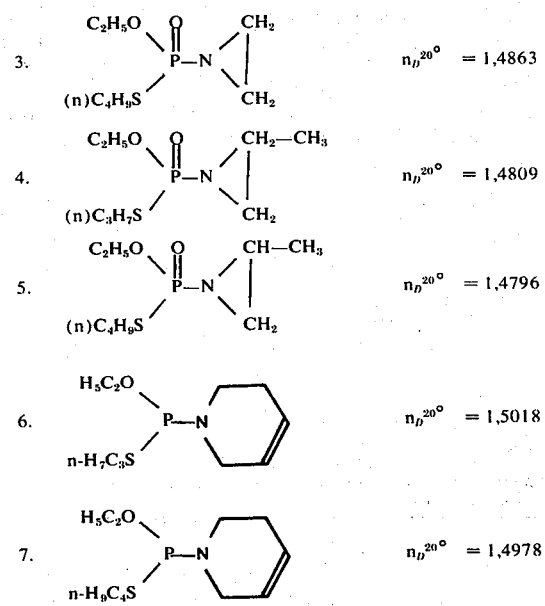

EXAMPLE 3

Nematocidal Test

The action against soil nematodes is tested by applying the active substance in the respective concentration to, and intimately mixing it with, soil infected with root gall nematodes (*Meloidogyne arenaria*). Immediately afterwards tomato cuttings are planted in the thus prepared soil test series A (Table 1), and after an interval of 8 days tomatoes are sown in test series B (Table 2).

The nematocidal action is assessed by counting the number of galls present in roots 28 days after the planting and sowing respectively.

Evaluation: 0 = complete nematocidal action, no attack
3 = no nematocidal action, same attack as control
1 and 2 = intermediate stages of attack.

TABLE 1

Test Series A
Concentration : 10 ppm
(ppm = parts of active substance in $10^6$ parts of diluent)

| Active Substance: | Nematocidal action |
|---|---|
| Compound 1 (according to the invention) | 0 |
| 1-(ethoxy-n-propylthio-phosphinyl)-dimethylamine (Dutch Pat. No. 6.602.588) | 2 |

TABLE 1-continued

Test Series A
Concentration : 10 ppm
(ppm = parts of active substance in $10^6$ parts of diluent)

| Active Substance: | Nematocidal action |
|---|---|
| 1-(dimethoxy-phosphinyl)-2-methyl-aziridine | 3 |
| 1-(dimethoxy-thiophosphinyl)-2-methyl-azaridine (known from German Offenlegungsschrift 2.011.092) | 3 |
| 1-(diethoxy-thiophosphinyl)-pyrrolidine (known from U.S. Pat. No. 3.511.633) | 3 |
| O,O-diethyl-O—2,4-dichlorophenyl-thio-phosphoric acid ester (known from U.S. Pat. No. 2.761.806 under the registered trademark "VC-13-Nemacide" of Virginia-Carolina Chem. Corp) | 3 |
| 3,5-dimethyl-2-thio-tetrahydro-2H—1,3,5-thiadiazine (known under the registered trademark "Dazomet") | 3 |

TABLE 2

Test Series B
Concentration : 10 ppm

| Active Substance: | Nematocidal action |
|---|---|
| Compound 1 (according to the invention) | 0 |
| 1-(ethoxy-n-propylthio-phosphinyl)-dimethylamine (Dutch Pat. No. 6.602.588) | 2 |
| 1-(dimethoxy-phosphinyl)-2-methyl-aziridine | 3 |
| 1-(dimethoxy-thiophosphinyl)-2-methyl-azaridine (known from German Offenlegungsschrift 2.011.092) | 3 |
| 1-(diethoxy-thiophosphinyl)-pyrrolidine (known from U.S. Pat. No. 3.511.633) | 3 |
| O,O-diethyl-O—2,4-dichlorophenyl-thio-phosphoric acid ester (known from U.S. Pat. No. 2.761.806 under the registered trademark "VC-13-Nemacide" of Virginia-Carolina Chem. Corp) | 3 |
| 3,5-dimethyl-2-thio-tetrahydro-2H—1,3,5-thiadiazine (known under the registered trademark "Dazomet") | 3 |

EXAMPLE 4

Action against rice stem borers

Eight rice plants with side-shoots were reared in two rows in soil covered with water (¼m² surface area) in a container made of asbestos-cement. Five stems at a time are inoculated on 3 infestation dates with a larva of Chilo suppressalis in the $L_1$ larval stage. The infestation dates are 2, 8, and 16 days after the addition of active substance granules in a concentration corresponding to 8 kg of active substance/ha. The activity control is carried out 10 days after each infestation date.

| Active substance | Mortality 2 days | 8 days | 16 days | Overall rating |
|---|---|---|---|---|
| No. 1 (according to the invention) | 5 | 7 | 8 | 7 |
| N—(2-methyl-4-chlorophenyl)-N',N'—dimethylformamidine (known | 4 | 6 | 6 | 6 |

Rating:    1 = no action
          9 = complete mortality
          2–8 = intermediate stages of action.

I claim:

1. A pesticidal composition for combating insects, acarids and nematodes which comprises (1) as active ingredient a pesticidally effect amount of a compound of the formula

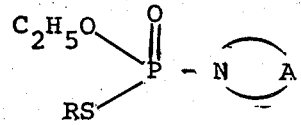

wherein R represents n-propyl or n-butyl, and A represents 2-butenylene or 2-pentenylene, and (2) a carrier.

2. A method for combating pests selected from the group consisting of insects, acarids and nematodes which comprises applying thereto a pesticidally effective amount of a compound of the formula

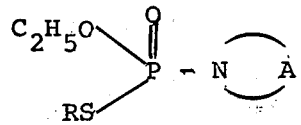

wherein R represents n-propyl or n-butyl, and A represents 2-butenylene or 2-pentenylene.

3. The method according to claim 2 in which the compound is

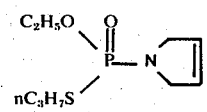

* * * * *